(12) United States Patent
Yang et al.

(10) Patent No.: US 11,938,308 B2
(45) Date of Patent: Mar. 26, 2024

(54) IMPLANTABLE MICRONEEDLE AND MANUFACTURING METHOD THEREFOR

(71) Applicant: SNVIA CO., LTD., Busan (KR)

(72) Inventors: Seung Yun Yang, Miryang-si (KR); Sang-Gu Yim, Busan (KR); Young Jun Hwang, Mungyeong-si (KR)

(73) Assignee: SNVIA CO., LTD., Busan (KR)

( * ) Notice: Subject to any disclaimer, the term of this patent is extended or adjusted under 35 U.S.C. 154(b) by 935 days.

(21) Appl. No.: 16/959,620

(22) PCT Filed: Jan. 17, 2019

(86) PCT No.: PCT/KR2019/000710
§ 371 (c)(1),
(2) Date: Jul. 1, 2020

(87) PCT Pub. No.: WO2019/143152
PCT Pub. Date: Jul. 25, 2019

(65) Prior Publication Data
US 2020/0368452 A1    Nov. 26, 2020

(30) Foreign Application Priority Data

Jan. 18, 2018 (KR) .................. 10-2018-0006765

(51) Int. Cl.
*A61M 37/00* (2006.01)
*A61M 5/32* (2006.01)
(Continued)

(52) U.S. Cl.
CPC ........... *A61M 5/3286* (2013.01); *B81B 1/008* (2013.01); *B81C 1/00111* (2013.01);
(Continued)

(58) Field of Classification Search
CPC .. A61M 2037/0046; A61M 2037/0053; A61M 2207/00; A61M 37/0015; B81B 2201/055; A61K 9/0021
See application file for complete search history.

(56) References Cited

U.S. PATENT DOCUMENTS 9,114,238 B2    8/2015 Singh et al.
2008/0269685 A1  10/2008 Singh et al.
(Continued)

FOREIGN PATENT DOCUMENTS

JP    2012025723    2/2012
JP    2013043034    3/2013
(Continued)

OTHER PUBLICATIONS

International Search Report and Written Opinion issued in Corresponding PCT Application No. PCT/KR2019/000710, dated May 2, 2019 (English Translation Provided).

*Primary Examiner* — Deanna K Hall
(74) *Attorney, Agent, or Firm* — NORTON ROSE FULBRIGHT US LLP

(57) ABSTRACT

The present invention provides an implantable microneedle and a manufacturing method therefor. An implantable microneedle according to the present invention comprises a coating layer for covering at least one part of the surface of a tip part of the microneedle. When exposed to moisture, the coating layer can be separated from the tip part of the microneedle and thus be implanted.

19 Claims, 5 Drawing Sheets

(51) Int. Cl.
*B81B 1/00* (2006.01)
*B81C 1/00* (2006.01)

(52) U.S. Cl.
CPC .... *A61M 2207/00* (2013.01); *B81B 2201/055* (2013.01); *B81B 2203/0361* (2013.01); *B81C 2201/0197* (2013.01)

(56) References Cited

U.S. PATENT DOCUMENTS

| | | |
|---|---|---|
| 2010/0221314 A1 | 9/2010 | Matsudo et al. |
| 2012/0004626 A1* | 1/2012 | Kuwahara ............... A61L 27/00 604/272 |
| 2014/0350457 A1* | 11/2014 | Douroumis ............ A61K 47/10 427/2.3 |
| 2015/0335872 A1 | 11/2015 | Yang et al. |
| 2016/0279401 A1 | 9/2016 | Schwab et al. |
| 2017/0258712 A1 | 9/2017 | Oomori et al. |
| 2018/0243543 A1 | 8/2018 | Baek et al. |

FOREIGN PATENT DOCUMENTS

| | | |
|---|---|---|
| JP | 2017144307 | 8/2017 |
| JP | 6304431 | 4/2018 |
| KR | 101692266 | 1/2017 |
| KR | 101776659 | 9/2017 |
| WO | WO 2009/051147 | 4/2009 |
| WO | WO 2016/084701 | 6/2016 |
| WO | WO 2017/090254 | 6/2017 |
| WO | WO 2017/104144 | 6/2017 |
| WO | WO 2019/143152 | 7/2019 |

* cited by examiner

[FIG. 1]
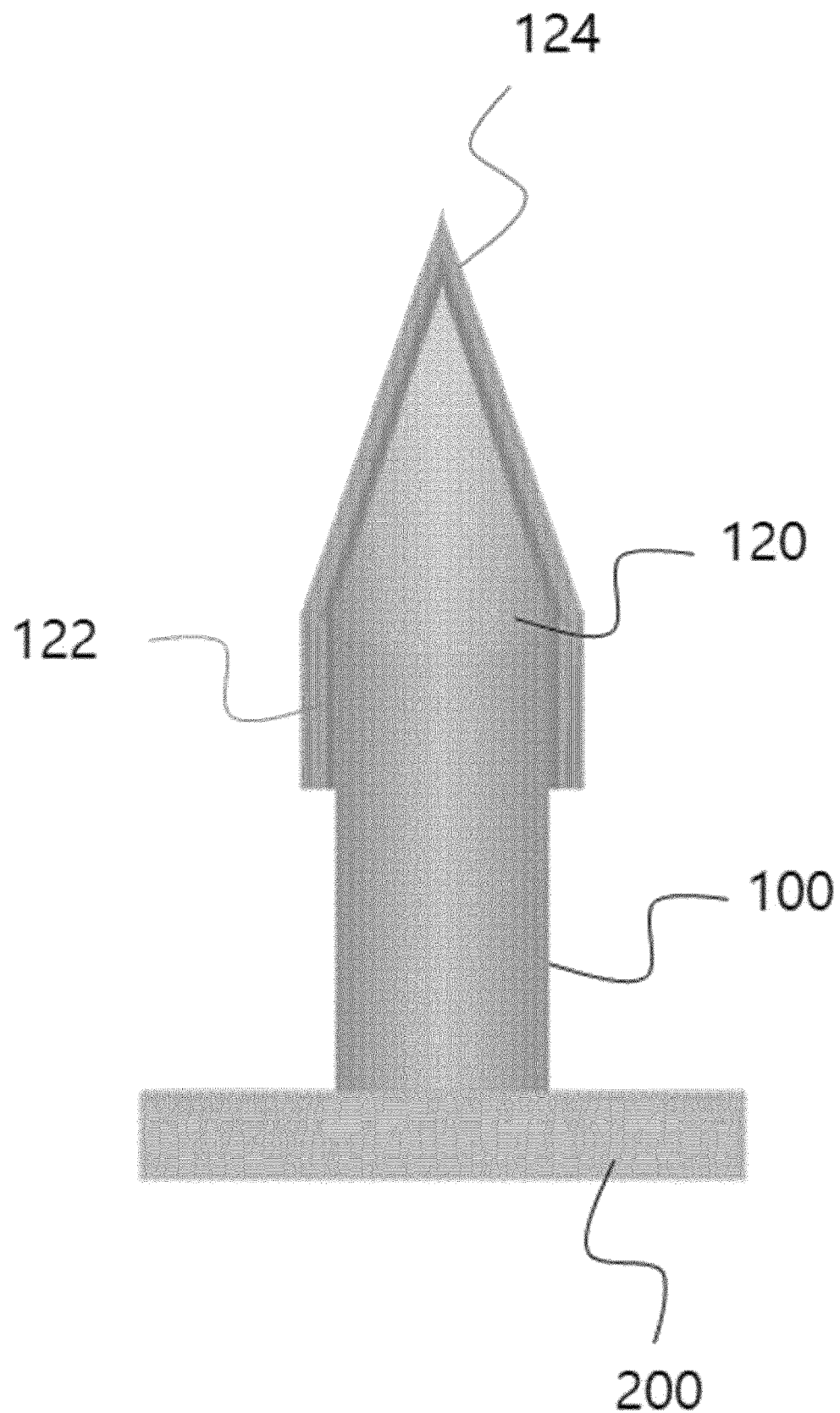

[FIG. 2]
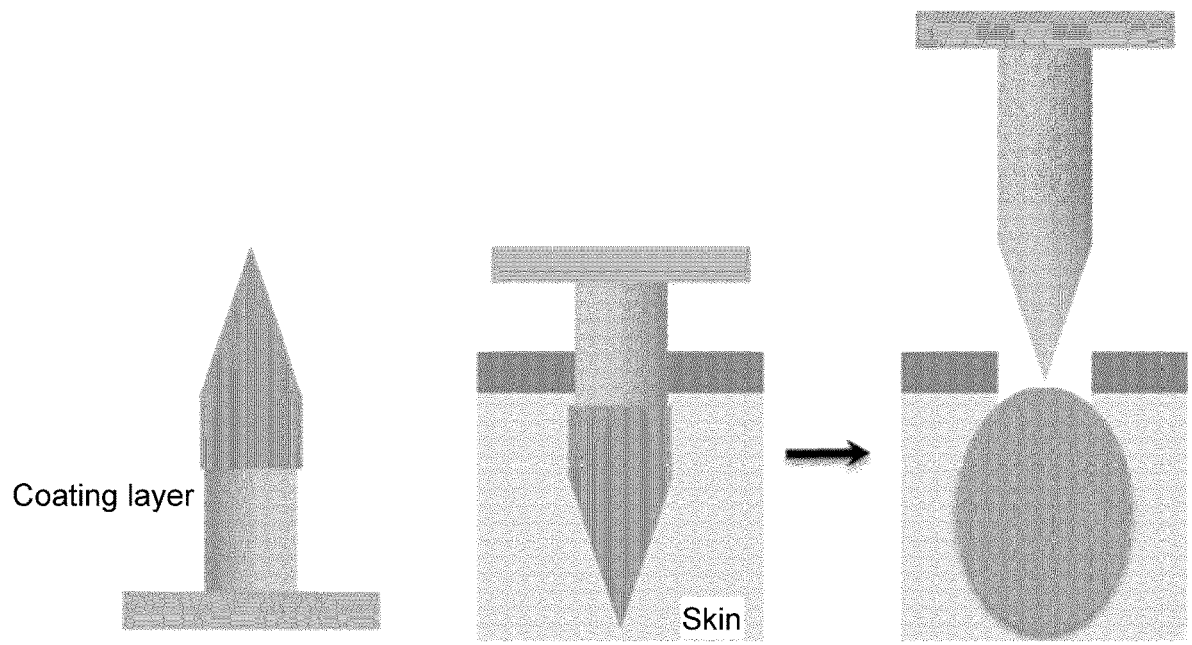

[FIG. 3]
(a)
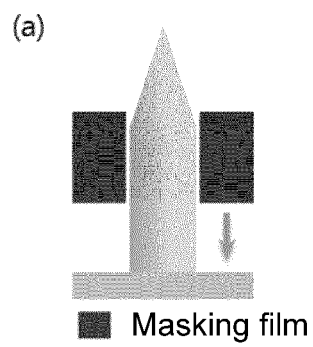
■ Masking film
(b)
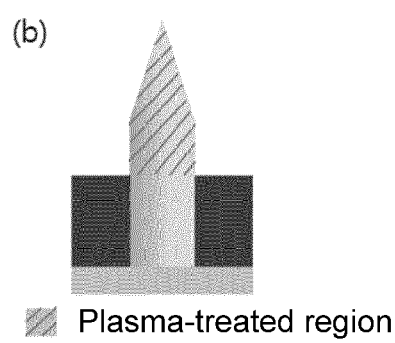
▨ Plasma-treated region
(c)
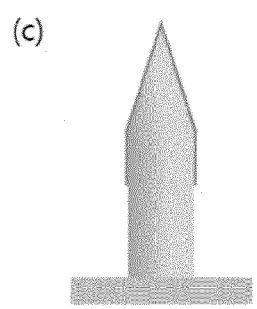
(d)
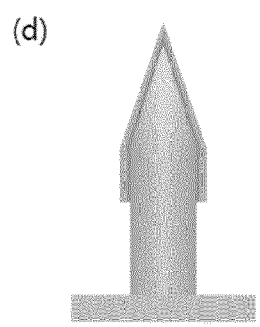

[FIG. 4A]
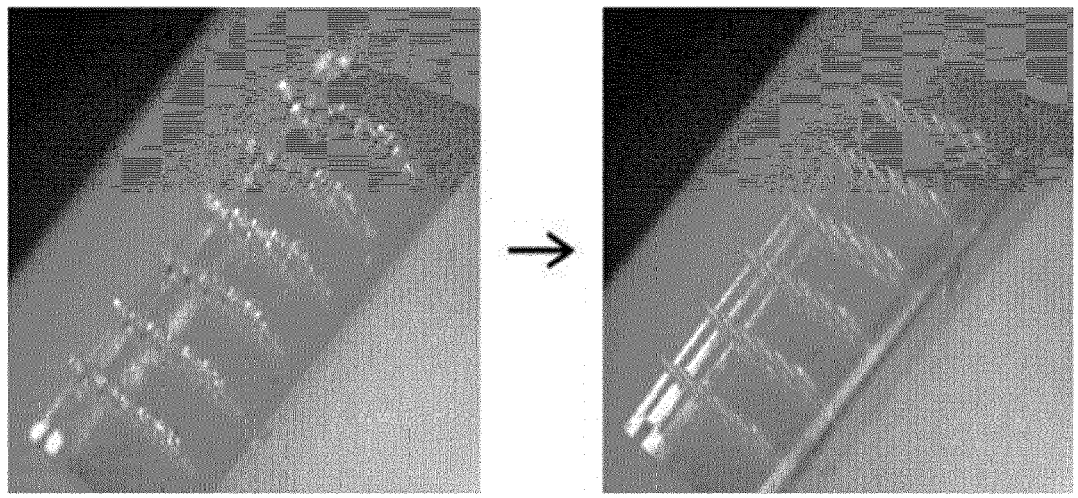
[FIG. 4B]
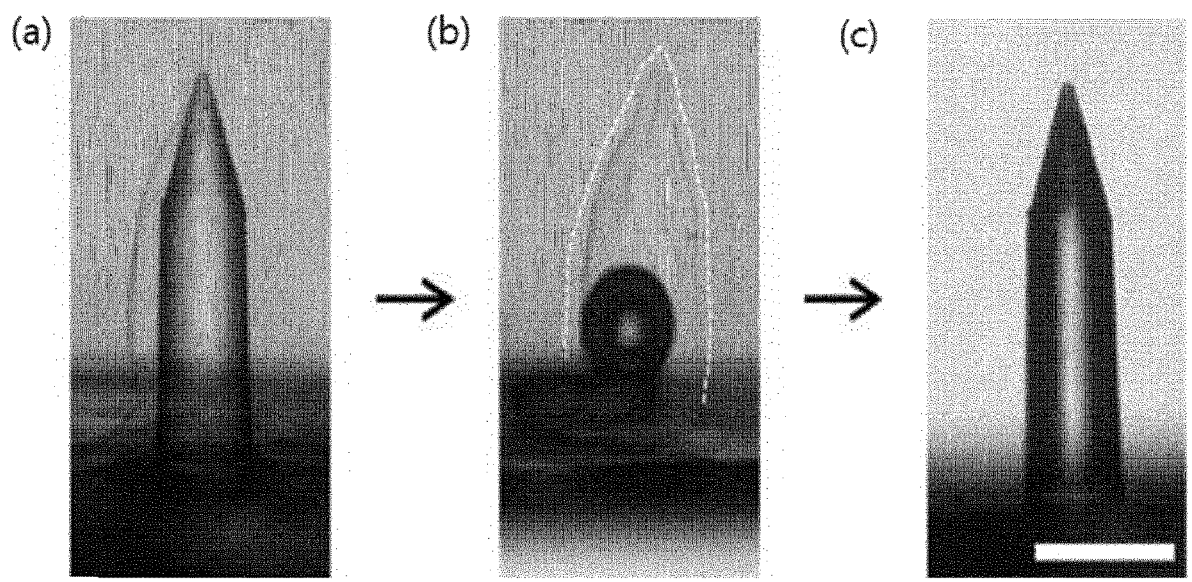

[FIG. 5A]
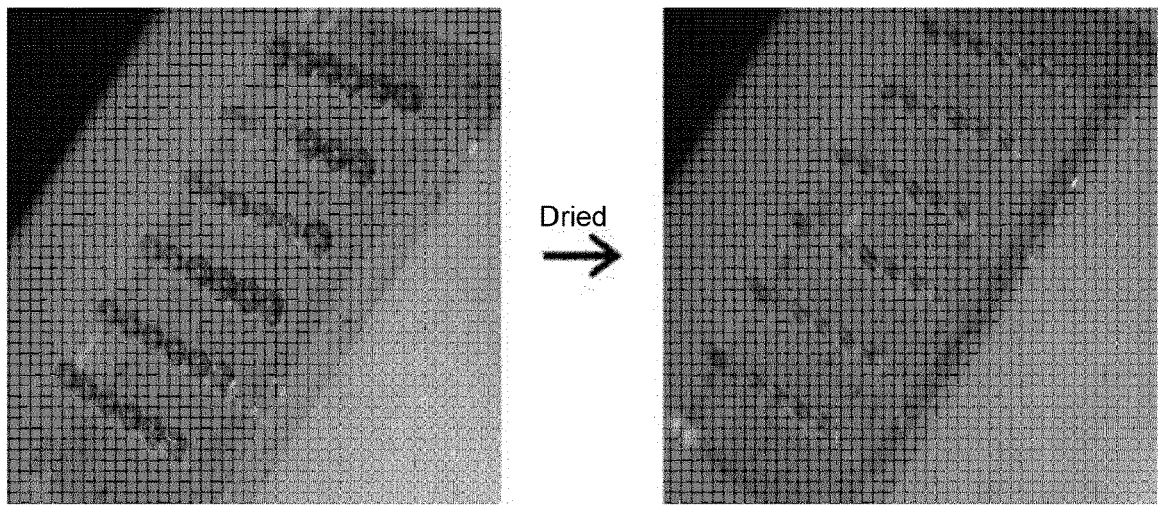
Dried →
[FIG. 5B]
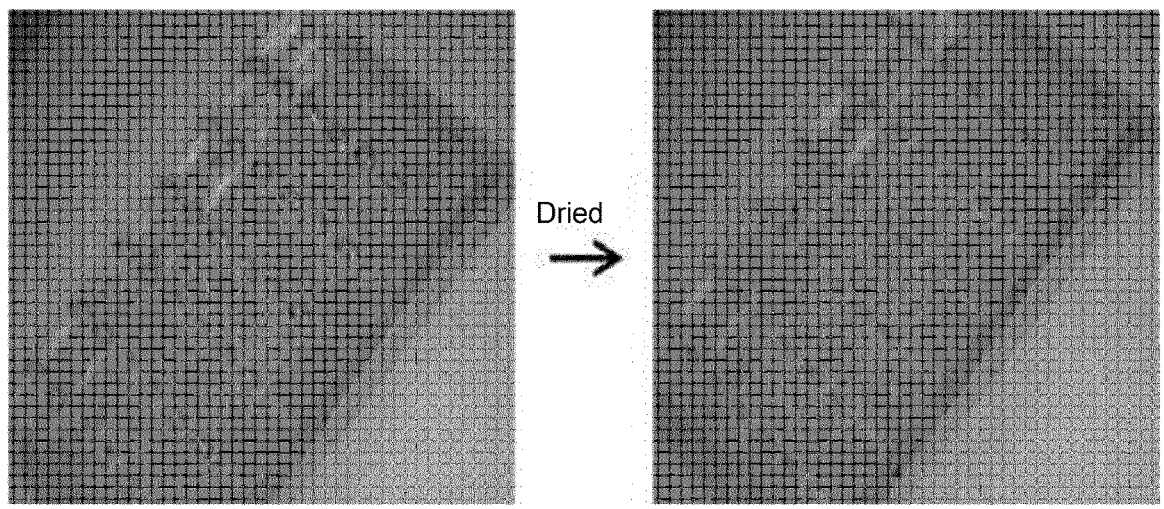
Dried →
[FIG. 5C]
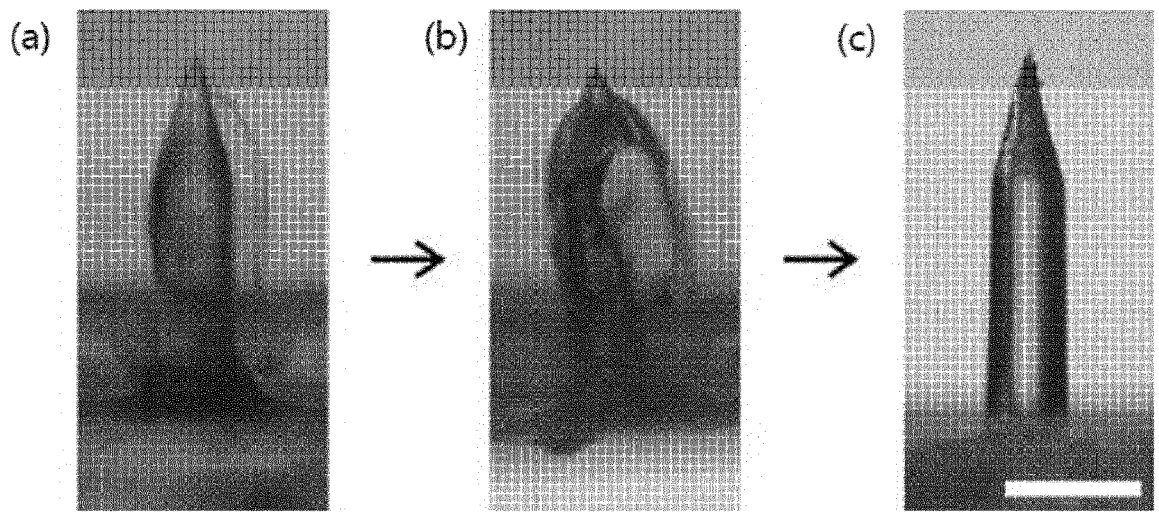
(a) → (b) → (c)

IMPLANTABLE MICRONEEDLE AND MANUFACTURING METHOD THEREFOR

CROSS REFERENCE TO RELATED APPLICATIONS

This application is a national phase under 35 U.S.C. § 371 of International Application No. PCT/KR2019/000710, filed Jan. 17, 2019, which claims the benefit of priority to Korean Patent Application Serial No. 10-2018-0006765, filed Jan. 18, 2018, the entire contents of each of which are hereby incorporated by reference in their entirety.

FIELD OF THE INVENTION

The present disclosure relates to a microneedle, and more specifically, to an implantable microneedle and a method for manufacturing the same.

DESCRIPTION OF RELATED ART

In order to manufacture a microneedle, a scheme in which a mold is filled with a polymer solution is generally used. However, in order to fill the polymer solution, a process should be performed in a vacuum state or a separate degassing process to remove air is required. Especially, a water-soluble polymer is not easily filled into a hydrophobic mold, and a needle shape of the microneedle is deformed during a process. Further, it is preferable that in a microneedle for drug delivery, the drug is applied only to a microneedle tip penetrating a tissue in order to effectively deliver the drug. However, when manufacturing a microneedle patch for drug delivery using the mold, the drug is contained in a patch in addition to the microneedle. Thus, it is difficult to deliver the drug quantitatively. Further, a large amount of the drug is lost. The method using the mold is inefficient and is economically expensive.

In view of the above fact, recently, a method of applying a polymer solution to a previously manufactured solid microneedle patch using a dip coating or a spray coating is used. In the dip coating method or the spray coating method, a large amount of the polymer solution is required to coat the microneedle therewith, and it is difficult to uniformly apply the polymer solution only to a tip.

Further, the conventional microneedle dissolves rapidly in a body, such that long-term release of the drug is not achieved. Skin damage or bacterial infection may occur due to attachment of the microneedle to the skin.

Accordingly, there is a need for research and development of a new type of a microneedle capable of quantitatively delivering a drug and preventing the risk of the skin damage or bacterial infection, and a method of manufacturing the same.

SUMMARY OF THE INVENTION

One purpose of the present disclosure is to provide a new type of a microneedle capable of quantitatively delivering a drug and preventing the risk of the skin damage or bacterial infection.

Another purpose of the present disclosure is to provide a method for manufacturing a new type of a microneedle capable of quantitatively delivering a drug and preventing the risk of the skin damage or bacterial infection.

A method of manufacturing an implantable microneedle to achieve one purpose of the present disclosure includes mounting a microneedle having a tip on a stage, and coating a swellable polymer solution on a surface of the tip of the microneedle while the stage is tilted at a predefined inclination, thereby forming a coating layer thereon.

A method of manufacturing an implantable microneedle to achieve another purpose of the present disclosure includes coating a swellable polymer solution to cover at least a portion of a surface of a tip of a microneedle having a cylindrical body and a conical tip, thereby forming a coating layer thereon.

A method of manufacturing an implantable microneedle to achieve still another purpose of the present disclosure includes coating an incompletely crosslinked swellable polymer solution on a surface of a tip of a microneedle so that at least a portion of an interface or a surface of the incompletely crosslinked swellable polymer is selectively dissolved in a short time in moisture, thereby to form a coating layer.

A method of manufacturing an implantable microneedle to achieve still another purpose of the present disclosure includes forming a sacrificial layer covering at least a portion of a surface of a tip of a microneedle, and coating a swellable polymer solution on the sacrificial layer, thereby forming a swellable polymer based coating layer.

An implantable microneedle according to the present disclosure includes a tip, and a coating layer covering at least a portion of a surface of the tip. When the coating layer is exposed to moisture, the coating layer is separated from the tip of the microneedle, so that the coating layer is implantable in the body.

According to the microneedle and the manufacturing method thereof according to the present disclosure, the microneedle in which the coating layer is formed only on the tip, and the coating layer is removable from the microneedle such that the coating layer is implantable in the body may be easily manufactured. In the microneedle according to the present disclosure, the coating layer is made of the swellable polymer. Thus, when the microneedle according to the present disclosure is inserted into the body, the swellable polymer based coating layer swells and is mechanically engaged with the skin tissue in the body and is fixed to the tissue. Then, when the microneedle is removed from the tissue, the coating layer may be separated from the microneedle and remain and be implantable in the body. Thus, the microneedle according to the present disclosure may be used as implantable drug delivery means or an implantable tissue adhesive. Further, the swellable polymer based coating layer may swell and thus fill a hole formed when the microneedle according to the present disclosure is inserted into the body, thereby to prevent tissue damage and secondary bacterial infection. In addition, the microneedle according to the present disclosure selectively carries a drug only in the coating layer formed on the tip, such that the drug is free of the body of the microneedle. Thus, the drug may be delivered quantitatively as desired. A large amount of the drug may not be required in manufacturing of the microneedle. This is more economical.

BRIEF DESCRIPTION OF THE DRAWINGS

FIG. 1 is a schematic diagram for illustrating a microneedle according to one embodiment of the present disclosure.

FIG. 2 is a schematic diagram for illustrating a microneedle according to one embodiment of the present disclosure.

FIG. 3 is a diagram for illustrating a method of manufacturing a microneedle according to the present disclosure according to one embodiment of the present disclosure.

FIG. 4a is a diagram for illustrating a microneedle according to Example 1 of the present disclosure.

FIG. 4b is a diagram for illustrating a microneedle according to Example 1 of the present disclosure.

FIG. 5a is a diagram for illustrating a microneedle according to Example 2 of the present disclosure.

FIG. 5b is a diagram for illustrating a microneedle according to Example 2 of the present disclosure.

FIG. 5c is a diagram for illustrating a microneedle according to Example 2 of the present disclosure.

DETAILED DESCRIPTIONS

Hereinafter, an embodiment of the present disclosure will be described in detail with reference to the accompanying drawings. The present disclosure may be variously modified and may take many forms. Thus, specific embodiments will be illustrated in the drawings and described in detail herein. However, the specific embodiments are not intended to limit the present disclosure thereto. It should be understood that all changes, equivalents thereto, or substitutes therewith are included in a scope and spirit of the present disclosure. In describing the drawing, similar reference numerals are used for similar components.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic diagram for illustrating a microneedle according to one embodiment of the present disclosure.

Referring to FIG. 1, a microneedle 100 according to the present disclosure has a needle shape having a tip 120 and has a coating layer 124 covering at least a portion of a surface of the tip 120.

The microneedle 100 has a micro needle shape. The microneedle 100 may be made of various materials such as polymers and metals. For example, the microneedle 100 may be microneedle 100 made of a biocompatible polymer. In this connection, when the microneedle 100 according to the present disclosure is made of a polymer, the microneedle 100 may have a strength such that the microneedle 100 does not break when being inserted into a body. The microneedle 100 according to the present disclosure may further include a patch portion 200 as a flat face portion on which the microneedle 100 is disposed. The patch portion 200 may mean a face portion that is not inserted into a skin but is in contact with and attached to the skin surface when the microneedle 100 is inserted into the skin. The patch portion 200 may exhibit elasticity and flexibility, and accordingly, a shape thereof may be changed to conform to a curved skin surface. Although not shown in the drawing, a plurality of microneedles 100 may be disposed on one face of the patch portion 200. Further, a single or multiple microneedles 100 may be disposed on one face of the patch portion 200 to constitute a microneedle patch 300 according to the present disclosure. In this connection, according to the present disclosure, the microneedle 100 may mean the single or multiple microneedles 100 disposed on one face of the patch portion 200 of the microneedle patch 300. Alternatively, the microneedle 100 may mean a single microneedle 100.

The tip 120 of the microneedle 100 refers a portion including a pointed portion or a cutting edge of the microneedle 100. In accordance with the present disclosure, the tip 120 may mean a region of about 50% or less of a total length of the microneedle 100. In one example, the microneedle 100 according to the present disclosure may have a cylindrical body and the tip formed at a top of the body. Specifically, for example, as shown in FIG. 1, the microneedle 100 according to the present disclosure may be in a form of a bullet or a pencil tip portion having a cylindrical body and a conical tip 120. In this connection, the tip 120 according to the present disclosure may mean the conical tip itself, or may mean to include the conical tip and a portion of the body attached thereto. FIG. 1 shows one preferred exemplary shape of the microneedle according to the present disclosure. However, the present disclosure is not necessarily limited thereto. The microneedle 100 according to the present disclosure may have a similar form thereto. The microneedle 100 according to the present disclosure in the form of the bullet has the cylindrical body and the conical tip, such that a sacrificial layer 122 and the coating layer 124 that cover at least a portion of the surface of the tip 120 of the microneedle 100 may be easily formed. More detailed descriptions thereof will be set forth later with reference to a manufacturing method of the microneedle according to the present disclosure.

The coating layer 124 according to the present disclosure refers to a thin film layer formed on the surface of the tip 120 while covering at least a portion of the surface of the tip 120 of the microneedle 100 according to the present disclosure. The coating layer 124 according to the present disclosure may be made of a crosslinkable swellable polymer. The swellable polymer means a polymer such as a hydrogel that absorbs a liquid such as water and thus increases in volume. In accordance with the present disclosure, the swellable polymer may be embodied as a biocompatible polymer having swellability and water solubility and/or biodegradability. For example, in accordance with the present disclosure, the swellable polymer may include a compound such as hyaluronic acid (HA), gelatin, chitosan, collagen, or chondroitin sulfate. The swellable polymer may be used in a crosslinked state or in a non-crosslinked state. In an example, the swellable polymer may contain an amine group (—$NH_2$) or a thiol group (—SH) which may be a functional group contained in the polymer itself or may be separately introduced thereto. When the swellable polymer contains the amine group or the thiol group, the swellable polymer may be crosslinked using genipin as a crosslinking agent. Further, a swelling rate and a dissolution rate of the coating layer 124 according to the present disclosure may be adjusted by controlling a molecular weight of the swellable polymer or by controlling a degree of crosslinking of the swellable polymer. For example, when the molecular weight of the swellable polymer is 600 k or greater, the coating layer 124 may be dissolved very slowly due to physical crosslinking between chains of the swellable polymer. Further, for example, when a physically, chemically or optically crosslinked swellable polymer forms the coating layer 124, the coating layer 124 may be swelled due to moisture and then slowly dissolved. Alternatively, the swellable polymer may be embodied as a non-crosslinked polymer or a polymer having a relatively low molecular weight. When the coating layer 124 is made of the non-crosslinked polymer or the low molecular weight polymer, the coating layer 124 may be swelled due to moisture and then quickly dissolved.

A case where the microneedle 100 according to the present disclosure is inserted into the skin will be described in more detail with reference to FIG. 2.

FIG. 2 is a schematic diagram for illustrating a microneedle according to one embodiment of the present disclosure.

Referring to FIG. 2 together with FIG. 1, in the microneedle 100 according to the present disclosure, the coating layer 124 made of the swellable polymer absorbs moisture in body fluid or blood in a skin tissue and thus swells and thus is brought into a firm mechanical engagement with the skin tissue and, accordingly, is fixed to the skin tissue. In this connection, when the molecular weight of the swellable polymer is high, the coating layer 124 may be dissolved more slowly, compared to a case when the swellable polymer of the low molecular weight is used. Thus, the molecular weight of the swellable polymer may be controlled to adjust the dissolution rate of the swellable polymer of the coating layer. In the same manner, the dissolution rate may be controlled depending on the degree of crosslinking of the swellable polymer.

Further, when the inserted microneedle 100 is removed from the skin, the microneedle 100 and the swelled coating layer 124 may be separated from each other due to the fixing force between the swelled coating layer 124 and the skin tissue and/or the dissolution of the swelled coating layer 124, so that the microneedle 100 is removed out of the body while the swelled coating layer 124 may remain in the body. That is, the swelled coating layer 124 may be implanted into the body. In this connection, for example, when the microneedle 100 according to the present disclosure is in the form of the bullet, the swelled coating layer 124 may be more easily separated from the microneedle 100. Detailed description thereof will be described later in more detail with reference to the manufacturing method of the microneedle according to the present disclosure.

Further, when the coating layer 124 swells, a fine hole formed in the skin tissue caused when inserting the microneedle 100 into the skin may be filled with the coating layer 124. Thus, skin tissue damage may be prevented or additional bacterial infection (secondary infection), etc. may be prevented.

In one example, the coating layer 124 may contain a functional substance such as a drug. For example, when the coating layer 124 contains the drug, the drug may be released into the skin tissue from the swelled coating layer 124. In this connection, the swelled coating layer 124 may control an release amount of the carried drug based on the degree of crosslinking of the swellable polymer thereof. In an example, the coating layer 124 made of the crosslinked swellable polymer may implement sustained release of the drug. That is, the coating layer 124 may deliver the drug into the body for a long time.

When the coating layer 124 contains the drug, the microneedle 100 according to the present disclosure may be used as implantable drug delivery means capable of implanting the swellable coating layer 124 into the body. Further, the microneedle 100 according to the present disclosure may be used as an implantable tissue adhesive that adheres tissues to each other in a wet environment. The tissue adhesive refers to a substance that adheres tissues to each other, and may be used for various purposes, including protecting wound areas, hemostasis, or bonding and sealing between the tissues. The microneedle 100 according to the present disclosure is inserted into the skin and absorbs moisture in bodily fluid in the skin surface or tissue, such that only the tip electively swells, thereby to achieve the firm mechanical engagement with the tissue, thereby to adhere the tissues to each other effectively in a wet environment. Therefore, the microneedle 100 according to the present disclosure may be used as the tissue adhesive that may be inserted into the tissues requiring the adhesion to each other and may quickly and easily adhere the tissues to each other via swelling of the coating layer 124. The microneedle 100 according to the present disclosure may be used not only for the skin, but also for soft tissues such as muscles and mucous membranes.

Further, in an example, the microneedle 100 according to the present disclosure may further include the sacrificial layer 122 between the surface of the tip 120 and the coating layer 124. In this case, the microneedle 100 according to the present disclosure may have a lamination structure between the sacrificial layer 122 covering at least a portion of the surface of the tip 120 and the coating layer 124 formed on the sacrificial layer 122 and covering at least a portion of the sacrificial layer 122. When the sacrificial layer 122 according to the present disclosure means a thin film layer made of a water-soluble compound that may be first dissolved in the moisture when being exposed to the moisture. The sacrificial layer 122 may be closely attached to the surface of the tip 120 of the microneedle 100 to form a thin film, thereby preventing direct contact between the microneedle 100 and the coating layer 124, thus preventing changes in properties of the coating layer 124 which may otherwise occur due to the microneedle 100. Further, when the coating layer 124 carries the drug, the sacrificial layer 122 may allow the coating layer 124 to maintain activity of the drug. Further, when the microneedle 100 is inserted into the skin, the sacrificial layer 122 may allow the coating layer 124 to be easily separated from the microneedle 100. Specifically, when the microneedle 100 according to the present disclosure is inserted into the skin, the sacrificial layer 122 has dissolved before the coating layer 124 has dissolved in the body fluid or blood in the skin tissue. Thus, an empty space (gap) is formed between the surface of the tip 120 of the microneedle 100 and the coating layer 124, such that the coating layer 124 may be easily separated from the microneedle 100. This will be described later in more detail.

The sacrificial layer 122 may be made of a water-soluble compound having a water solubility at which the compound is rapidly dissolved in the moisture. In this connection, the material of the sacrificial layer 122 may be capable of facilitating formation of the coating layer 124 on the sacrificial layer 122. In one example, the material of the sacrificial layer 122 may be a monosaccharide or a water-soluble polymer. In order that the sacrificial layer 122 quickly dissolves to quickly separate the coating layer 124 from the microneedle 100, the material of the sacrificial layer 122 may include the monosaccharide or the water-soluble polymer having a molecular weight of less than 10 K which may be rapidly dissolved in moisture such as body fluid or blood. In an example, sucrose may be used as the monosaccharide forming the sacrificial layer 122 according to the present disclosure. When the sacrificial layer 122 according to the present disclosure is made of the monosaccharide or the low molecular weight water-soluble polymer, the dissolution rate thereof may vary depending on the thickness of the sacrificial layer 122. However, generally, an entirety of the sacrificial layer 122 may dissolve within 10 minutes to allow the coating layer 124 to be separated from the microneedle 100.

When the microneedle 100 according to the present disclosure is inserted into the body, the coating layer 124 made of the swellable polymer swells due to the moisture in the body fluids or blood and thus mechanically engages with the skin tissue. In this connection, when the sacrificial layer 122 is present, the sacrificial layer 122 has been dissolved and disappeared before the swellable polymer of the coating layer 124 has been dissolved, thereby to form the empty space between the microneedle 100 and the coating layer 124. Therefore, when the inserted microneedle 100 is removed from the skin, the separation between the microneedle and the coating layer 124 is more easily achieved via the gap between the microneedle 100 and the coating layer 124, such that only the microneedle 100 is removed from the skin while the swelled coating layer 124 may be left in the skin tissue. That is, the coating layer 124 may be more easily separated from the microneedle 100 according to the present disclosure such that the coating layer 124 may be implanted into the body. In one example, for example, when the microneedle 100 according to the present disclosure is in the form of the bullet, the swelled coating layer 124 may be more easily separated from the microneedle 100. Detailed description thereof will be described later in more detail with reference to the manufacturing method of the microneedle according to the present disclosure.

Hereinafter, the manufacturing method of the implantable microneedle according to the present disclosure will be described in detail with reference to FIG. 1 and FIG. 2.

The manufacturing method of the implantable microneedle according to one embodiment of the present disclosure may include mounting the microneedle 100 having the tip 120 on a stage, and coating the swellable polymer solution on the tip 120 of the microneedle 100 while the stage is inclined at a predetermined inclination, thereby to form the coating layer 124.

The microneedle 100 and the swellable polymer are substantially the same as those as described above with reference to the microneedle 100 according to the present disclosure. Thus, detailed descriptions thereof will be omitted, and differences between descriptions of the implantable microneedle and the manufacturing method of the implantable microneedle will be mainly described later.

When the swellable polymer solution is coated on the tip 120 of the microneedle 100 while the stage on which the microneedle 100 is tilted at a predetermined inclination, the inclination of the tip 120 of the microneedle 100 decreases, and thus the coating of the solution thereon may be facilitated. This may prevent the swellable polymer solution from flowing downwards along the microneedle 100, so that the swellable polymer based coating layer 124 may be more easily formed thereon. In this connection, for example, the inclination may be greater than 0° and lower than 90°, and may be preferably 45°.

Further, according to one embodiment of the present disclosure, when coating the swellable polymer solution while the microneedle 100 is tilted, the swellable polymer solution may not be uniformly applied onto an entire face of the tip 120 of the microneedle 100, but may be selectively coated only on a portion of the tip such that a relatively large amount of the solution may be coated on the portion. The formed coating layer 124 may not have a uniform thickness on the entire surface of the tip 120 of the microneedle 100, and the larger amount thereof may exist only on the portion of the tip 120. That is, an asymmetric swellable polymer based coating layer 124 may be formed on the surface of the tip 120 of the microneedle 100. Thus, when being inserted into the body, the asymmetric swellable polymer based coating layer 124 may swell better due to the asymmetric structure of the swellable polymer based coating layer 124, and may more firmly engage with the tissue. Furthermore, when the microneedle 100 is removed from the skin, the swellable polymer based coating layer 124 may be detached from the microneedle 100 more easily.

In one example, the coating of the swellable polymer solution may be carried out in a drip scheme. In this case, a dispenser may be used. Further, the applied swellable polymer solution may be further crosslinked physically, chemically or optically as required.

In one example, for example, the method may further include, before forming the coating layer 124, forming the sacrificial layer 122 on the surface of the tip 120 of the microneedle 100. Alternatively, the coating layer 124 may be formed on the surface of the tip 120 of the microneedle 100 on which the sacrificial layer 122 is already formed. In this connection, the sacrificial layer may be made of a monosaccharide or a water-soluble polymer having a molecular weight of less than 10k, as described above with reference to the microneedle according to the present disclosure.

Further, the manufacturing method of the implantable microneedle according to another embodiment of the present disclosure includes coating the swellable polymer solution on at least a portion of the surface of the tip 124 of the microneedle 100 having a cylindrical body and a conical tip, thereby to forming the coating layer 124.

The microneedle 100 and the swellable polymer are substantially the same as those described above with refence to the microneedle 100 according to the present disclosure. Thus, detailed descriptions thereof will be omitted, and differences between descriptions of the implantable microneedle and the manufacturing method of the implantable microneedle will be mainly described later.

When the swellable polymer solution is coated on the microneedle 100 having the bullet-like shape having the cylindrical body and the conical tip, the coating layer 124 may be more stably coated. Specifically, important factors in coating the polymer solution on the microneedle 100 are an contact area, and a sliding angle or an inclination of a contact surface which may be related to an adhesion force required between the solution and the contact surface. In this connection, the smaller the contact area or the larger the inclination, the greater a gravity of a liquid droplet compared to the adhesion force to the surface, such that a stable coating may not be achieved and the liquid may flow down along the inclined surface (See Equation 1).

$$F_{adhesion} = \frac{\rho V g \sin\theta_\theta}{\pi d_w}$$ Equation 1

(In Equation 1, ρ refers to a density of the solution, V refers to a volume of a droplet of the solution, g refers to a gravitational acceleration, $\theta_2$ refers to an inclined angle, and $d_w$ refers to a contact area of the solution.)

That is, when a microneedle having a bullet shape having a cylindrical body and a conical tip and a microneedle having a cone-like shape have the same length, a tip of the microneedle having the bullet shape has a lower inclination and a larger contact area than those in the microneedle having the cone-like shape. Thus, the solution may be more stably coated on the surface of the tip of the microneedle having the bullet shape. Therefore, according to the present disclosure, the swellable polymer based coating layer 124 may be coated on the tip of the microneedle 100 having the bullet shape having the cylindrical body and the conical tip, such that the swellable polymer solution may be prevented from flowing downwards along the body of the microneedle 100 and thus the coating layer 124 may be formed only on the surface of the tip 120 of the microneedle 100.

Further, when the microneedle 100 has a bullet-like shape having a cylindrical body and a conical tip, the microneedle 100 may be more easily separated from the swelled coating layer 124 when it is inserted into the body and then removed therefrom. In other words, because the microneedle has the cylindrical body and the conical tip, the swelled coating layer 124 may be separated more easily from the microneedle due to the moisture.

In one example, for example, forming the coating layer 124 by coating the swellable coating layer solution on the surface of the tip 124 of the microneedle 100 having the cylindrical body and the conical tip according to another embodiment according to the present disclosure may include mounting the microneedle 100 having the tip 120 on a stage, and coating the swellable polymer solution on the tip 120 of the microneedle 100 while the stage is inclined at a predetermined inclination, thereby to form the coating layer 124, as described with reference to the manufacturing method of the implantable microneedle according to one embodiment of the present disclosure.

Further, as described above with reference to the manufacturing method of the implantable microneedle according to one embodiment of the present disclosure, in one example, the coating of the swellable polymer solution may be performed in a drip scheme. In this case, a dispenser may be used. Further, the applied swellable polymer solution may be further crosslinked physically, chemically or optically as required.

In addition, in an example, the method may further include, before forming the coating layer 124, forming the sacrificial layer 122 on the surface of the tip 120 of the microneedle 100. Alternatively, the coating layer 124 may be formed on the surface of the tip 120 of the microneedle 100 on which the sacrificial layer 122 is already formed. In this connection, the sacrificial layer may be made of a monosaccharide or a water-soluble polymer having a molecular weight of smaller than 10k, as described above with reference to the manufacturing method of the microneedle according to the present disclosure.

The manufacturing method of the implantable microneedle according to still another embodiment of the present disclosure may include forming the coating layer 124 by coating an incompletely crosslinked swellable polymer solution on the surface of the tip 120 of the microneedle 100 having the tip 120 such that at least a portion of an interface or a surface of the applied incompletely crosslinked swellable polymer solution may be selectively dissolved in a short time in moisture.

The microneedle 100 and the swellable polymer are substantially the same as those described above with refence to the microneedle 100 according to the present disclosure. Thus, detailed descriptions thereof will be omitted, and differences between descriptions of the implantable microneedle and the manufacturing method of the implantable microneedle will be mainly described later.

In accordance with the present disclosure, the incompletely cross-linked swellable polymer solution composed so that at least a portion of the interface or the surface thereof is soluble in water in a short time may mean a solution containing a swellable polymer having a cross-linking degree controlled such that, after swelling thereof, the at least a portion of the interface or the surface thereof may be dissolved within a short time in water. In this connection, the short time may mean a time within 1 hour after the insertion of the microneedle into the body, preferably, a time within 30 minutes, more preferably, a time within 15 minutes after the insertion of the microneedle into the body. The short time may vary depending on the selected polymer. However, the present disclosure is not necessarily limited thereto. According to the present disclosure, when coating the tip 120 of the microneedle 100 with the incompletely crosslinked swellable polymer solution composed so that at least a portion of the interface or the surface thereof is soluble in water in a short time, the swellable polymer forming the coating layer 124 is not sufficiently crosslinked, and thus the surface of the coating layer 124 is rapidly dissolved in the moisture when the microneedle 100 is inserted into the body. Accordingly, the coating layer 124 may be easily separated from the microneedle 100.

In this connection, in one example, the incompletely cross-linked swellable polymer solution composed so that at least a portion of the interface or the surface thereof is soluble in water in a short time may contain a swellable polymer having a molecular weight of 600 k or smaller. For example, when the molecular weight thereof is 600 k or greater, the dissolution occurs relatively slowly due to the physical crosslinking between the polymer molecular chains. Thus, preferably, the swellable polymer may have a molecular weight of 600 k or smaller. The present disclosure is not limited thereto.

In one example, forming the coating layer 124 by coating the incompletely crosslinked swellable polymer solution on the surface of the tip 120 of the microneedle 100 having the tip 120 such that at least a portion of the interface or the surface of the applied incompletely crosslinked swellable polymer solution may be selectively dissolved in a short time in moisture according to still another embodiment of the present disclosure may include mounting the microneedle 100 having the tip 120 on a stage, and coating the incompletely crosslinked swellable polymer solution composed so that at least a portion of the interface or the surface thereof is soluble in water in a short time on the tip 120 of the microneedle 100 while the stage is inclined at a predetermined inclination, thereby to form the coating layer 124, as described with reference to the manufacturing method of the implantable microneedle according to one embodiment of the present disclosure. In this connection, the incompletely crosslinked swellable polymer solution composed so that at least a portion of the interface or the surface thereof is soluble in water in a short time may be applied on the tip 124 of the microneedle 100 having the bullet shape having the cylindrical body and the conical tip, as described with reference to the manufacturing method of the implantable microneedle according to another embodiment of the present disclosure. In this connection, the incompletely crosslinked swellable polymer solution composed so that at least a portion of the interface or the surface thereof is soluble in water in a short time may be applied on the tip 124 of the microneedle 100 having the bullet shape having the cylindrical body and the conical tip while the microneedle 100 is in a tilted state at a predetermined inclination.

Further, as described above with reference to the manufacturing method of the implantable microneedle according to one embodiment or another embodiment of the present disclosure, for example, the coating of the swellable polymer solution may be performed in a drip scheme. In this case, a dispenser may be used. Further, the applied swellable polymer solution may be further crosslinked physically, chemically or optically as required.

In addition, in an example, the method may further include, before forming the coating layer 124, forming the sacrificial layer 122 on the surface of the tip 120 of the microneedle 100. Alternatively, the coating layer 124 may be formed on the surface of the tip 120 of the microneedle 100 on which the sacrificial layer 122 is already formed. In this connection, the sacrificial layer may be made of a monosaccharide or a water-soluble polymer having a molecular weight of smaller than 10k, as described above with reference to the manufacturing method of the microneedle according to the present disclosure.

Further, the manufacturing method of the implantable microneedle according to still another embodiment of the present disclosure may include forming the sacrificial layer 122 covering at least a portion of the surface of the tip 120 of the microneedle 100 and coating the swellable polymer solution on the sacrificial layer 122, thereby coating the swellable polymer based coating layer 124.

The microneedle 100 and the swellable polymer are substantially the same as those described above with refence to the microneedle 100 according to the present disclosure. Thus, detailed descriptions thereof will be omitted, and differences between descriptions of the implantable microneedle and the manufacturing method of the implantable microneedle will be mainly described later.

In this connection, the method may further include, prior to the step of forming the swellable polymer based coating layer 124, coating a sacrificial layer solution containing a water-soluble compound on the surface of the tip 120 of the microneedle 100 having the tip 120 to form the sacrificial layer 122 thereon. In this way, the microneedle 100 including the sacrificial layer 122 covering at least a portion of the surface of the tip 120 may be prepared.

The sacrificial layer solution forming the sacrificial layer may contain the water-soluble compound such as a monosaccharide or a low molecular weight water-soluble polymer. When the swellable polymer solution is applied on the sacrificial layer, the water-soluble compound may allow a portion of the sacrificial layer to be dissolved to improve viscosity of the swellable polymer solution. In one example, the water-soluble compound may be sucrose. In an example, the sacrificial layer solution may be an aqueous sucrose solution. In this connection, the sucrose aqueous solution may preferably have a viscosity value of 0.95 to 1.3 cp, and a concentration of 1 to 5 wt %. In this connection, a volume of the sucrose aqueous solution forming the sacrificial layer may be about 0.05 to 0.3 μl. The above specific viscosity value, concentration and volume are exemplarily mentioned. The present disclosure is not necessarily limited thereto. The viscosity value, concentration and volume are allowed as long as the selected water-soluble compound solution is coated in a drip manner.

According to the present disclosure, when applying the swellable polymer solution on the sacrificial layer 122 containing the water-soluble compound, the swellable polymer solution may not flow downwards along the microneedle 100 and may be closely coated on the surface of the sacrificial layer 122 via a surface tension or the like. Further, the sacrificial layer 122 contains the water-soluble compound capable of allowing the dissolving of at least a portion of the sacrificial layer 122 when applying the swellable polymer solution on the sacrificial layer 122. Thus, when the swellable polymer solution is applied thereon, the at least a portion of the surface of the sacrificial layer 122 may be temporarily dissolved in the swellable polymer solution to improve the viscosity of the swellable polymer solution. Thus, the swellable polymer solution may not flow downwardly due to the viscosity increase and may be reliably coated on the sacrificial layer 122. That is, the coating layer 124 may be coated only on the tip 120 of the microneedle 100. Therefore, according to the present disclosure, after the sacrificial layer 122 is formed, the coating layer 124 may be easily formed on the sacrificial layer 122 without a treatment process such as a separate plasma treatment. For example, when the sacrificial layer 122 is made of sucrose, the swellable polymer capable of forming the coating layer 120 based on the above mechanism may include crosslinked or non-crosslinked gelatin, chitosan, chondroitin sulfate, hyaluronic acid, etc. In this connection, the swellable polymer may have a functional group introduced therein or may be copolymerized with another polymer.

In one example, according to still another embodiment of the present disclosure, forming the sacrificial layer 122 covering at least a portion of the surface of the tip 120 of the microneedle 100 and coating the swellable polymer solution on the sacrificial layer 122, thereby coating the swellable polymer based coating layer 124 may be performed while the microneedle 100 is mounted on the stage which is tilted at a predetermined inclination, as described above with reference to the manufacturing method of the implantable microneedle according to one embodiment of the present disclosure. Furthermore, prior to the step of forming the swellable polymer based coating layer 124, the coating of the sacrificial layer solution containing the water-soluble compound on the surface of the tip 120 of the microneedle 100 having the tip 120 to form the sacrificial layer 122 thereon may be performed while the microneedle 100 is mounted on the stage which is tilted at a predetermined inclination, as described above with reference to the manufacturing method of the implantable microneedle according to one embodiment of the present disclosure. In this connection, the microneedle 100 may include the microneedle 100 having the bullet shape having the cylindrical body and the conical tip, as described with reference to the manufacturing method of the implantable microneedle according to another embodiment of the present disclosure. In this connection, the forming the sacrificial layer 122 may be applied on the tip 124 of the microneedle 100 having the bullet shape having the cylindrical body and the conical tip while the microneedle 100 is in a tilted state at a predetermined inclination.

Further, as described above with reference to the manufacturing method of the implantable microneedle according to one embodiment or another embodiment of the present disclosure, for example, the coating of the sacrificial layer solution and/or the coating of the swellable polymer solution may be performed in a drip scheme. In this case, a dispenser may be used. Further, the applied swellable polymer solution may be further crosslinked physically, chemically or optically as required.

In addition, the swellable polymer may be the incompletely crosslinked swellable polymer composed such that at least a portion of the interface or the surface thereof is soluble in a short time in water, as described above with reference to the manufacturing method of the implantable microneedle according to another embodiment of the present disclosure. In this connection, the sacrificial layer 122 may have been dissolved before the coating layer 124 made of the swellable polymer has been dissolved.

In addition, in the manufacturing methods of the implantable microneedle according to the embodiments of the present disclosure as described above, the surface of the tip 120 of the microneedle 100 may be selectively hydrophilized before forming the coating layer 124 thereon, or before forming the sacrificial layer 122 thereon when the sacrificial layer 122 is included therein.

In this connection, only the tip 120 of the microneedle 100 may be exposed such that only the exposed tip 120 of the microneedle is selectively hydrophilized. In this connection, various hydrophilic surface treatment schemes may be used. For example, the surface of the exposed tip 120 of the microneedle may contact a solution of a substance that may chemically react with the tip surface of the microneedle 100 to selectively hydrophilize the tip 120 of the microneedle. Alternatively, the hydrophilic treatment may be a plasma treatment.

FIG. 3 shows a diagram for illustrating a manufacturing method of a microneedle according to the present disclosure in a specific embodiment in which, the surface of the tip 120 of the microneedle 100 is selectively subjected to the plasma treatment, and then the sacrificial layer 122 is formed on the treated tip surface and then the swellable polymer is formed on the sacrificial layer 122.

Specifically, in FIG. 3, (a) is a schematic diagram for illustrating attachment of a masking film to the microneedle, (b) is a schematic diagram for illustrating selective plasma treatment of the microneedle, (c) is a schematic diagram for illustrating formation of the sacrificial layer, and (d) is a schematic diagram for illustrating formation of the coating layer.

Referring to FIG. 3 together with FIG. 1 and FIG. 2, in order to selectively plasma-treat the microneedle 100, only an exposed tip 120 of the microneedle 100 may be selectively plasma-treated. The exposure of the tip 120 of the microneedle 100 may be achieved by placing a masking film on an overall surface of the microneedle 100 excluding the tip 120 (See (a) and (b) in FIGS. 3).

The plasma may be capable of forming hydrophilic functional groups such as a hydroxyl group (—OH), and a carboxyl group (—COOH) on the surface of the tip 120 of the microneedle 100. That is, the plasma may be capable of hydrophilizing the surface of the tip 120. In one example, the plasma capable of hydrophilizing the surface of the tip may be an oxygen plasma, an argon plasma, or an ammonia plasma. An example of the present disclosure has been described in which the plasma is sued for the hydrophilic surface treatment. However, the present disclosure is not limited thereto.

For example, when the microneedle 100 according to present disclosure includes both the sacrificial layer 122 and the swellable coating layer 124 as shown in the drawing, the sacrificial layer solution containing the water-soluble compound for forming the sacrificial layer 122 may be easily coated on the hydrophilized surface of the tip 120 of the microneedle 100 (See (c) in FIG. 3). The swellable polymer solution may be coated on the formed sacrificial layer 122 without further treatment (See (d) in FIG. 3).

In one example, although not shown in the drawing, the implantable microneedle 100 according to the present disclosure does not include the sacrificial layer 122. In this case, adjusting a time to treat the surface of the tip 120 of the microneedle 100 with the plasma may control the adhesion between the surface of the tip 120 of the microneedle 100 and the coating layer 124. Accordingly, the surface of the tip 120 may be plasma-treated so that the coating layer 124 may be more easily coated on the tip 120 of the microneedle 100, and at the same time, the coating layer is well detached from the microneedle 100 when the microneedle 100 is inserted into the body. In this connection, the adhesive force between the surface of the tip 120 of the microneedle 100 and the coating layer 124 may be proportional to the plasma treatment time.

Further, in an example, in the examples according to the present disclosure, the swellable polymer solution may be coated at a viscous, a concentration, and a volume at which the swellable polymer solution may be coated in a drip manner. For example, a viscosity value may be 10 to 20,000 cp, and a volume may be 0.1 to 0.4 µl. The above specific viscosity value, concentration, and volume are exemplarily mentioned. However, the present disclosure is not necessarily limited thereto. The viscous, the concentration, and the volume may be limited particularly as long as the selected polymer solution may be coated in a dripping manner. For example, when using a hyaluronic acid having a molecular weight of 600 k as the swellable polymer, the hyaluronic acid solution containing the same may preferably have a viscosity value of 20 to 20,000 cp, and a concentration of 0.25 to 3 wt %. It may be desirable that the volume of the dripped hyaluronic acid solution may be 0.15 to 0.4 µl. Further, in an example, when using cross-linked gelatin using the swellable polymer, it may be desirable to coat the crosslinked gelatin at a concentration of about 5 wt %, at a viscosity value of 30 to 100 cp, and at a volume of about 0.1 to 0.4 µl.

In addition, the swellable polymer solution may contain a functional substance such as a drug. When the coating layer 124 is made of a swellable polymer solution containing a drug, the microneedle 100 is inserted into the skin tissue, and thus the drug may be released from the coating layer 124. The amount of the drug released from the microneedle 100 may be controlled by adjusting the amount of the drug added to the swellable polymer solution, by controlling the number of times the swellable polymer is coated on the surface of the tip 120 of the microneedle 100, or by controlling the degree of crosslinking of the swellable polymer. In this connection, for example, in order to slowly dissolve the coating layer 124, the coating layer 124 may have an increased degree of crosslinking by physically, chemically, or optically crosslinking the dripped swellable polymer solution. Alternatively, the coating layer 124 may be formed by dripping a crosslinked swellable polymer solution. Further, in one example, in order to rapidly dissolve the coating layer 124, a non-crosslinked swellable polymer may be used.

According to the present disclosure, when selectively coating the swellable polymer solution containing a functional substance such as a drug only on the tip 120 of the microneedle 100, the functional substance may be contained only on the tip 120 of the microneedle 100. Accordingly, the amount of the functional substance to be delivered may be delivered into the body without loss thereof, thereby to deliver the functional substance efficiently and economically without wasting the functional substance.

Hereinafter, examples of a microneedle according to the present disclosure, a manufacturing method thereof, and a patch including the same will be described in more detail.

First, a microneedle patch having a microneedle having a bullet-like form was manufactured using poly(lactic-co-glycolic acid) (PLGA) as a biocompatible polymer having a strength at which the microneedle does not break when being inserted into the body. Then, a masking film was placed on the microneedle, and oxygen plasma was selectively applied only onto the tip surface of the microneedle.

Then, the coating layer was formed using 600 k hyaluronic acid as a polymer. Specifically, a microneedle patch including a microneedle having the tip as selectively plasma-treated was mounted on the stage, and the stage was tilted at an angle of about 45°. A hyaluronic acid solution containing the hyaluronic acid having 600 k of a molecular weight which was dissolvable in moisture in a short time was dripped onto the tip of the microneedle. Then, the solution was dried at room temperature to manufacture a microneedle patch (hereinafter, microneedle 1) according to Example 1 of the present disclosure.

FIG. 4a is a diagram to illustrate the microneedle according to Example 1 of the present disclosure and shows a coating layer obtained by dropping the hyaluronic acid solution only on the plasma-treated tip surface of the microneedle and drying the solution at room temperature.

Referring to FIG. 4a, it may be identified that after dropping the hyaluronic acid solution on the tip surface of the microneedle according to the present disclosure, the hyaluronic acid solution does not flow downwardly along the microneedle such that a shape of the dropped solution is maintained. It may be identified that after drying the dropped solution at room temperature, the coating layer is in close contact with the tip of the microneedle and is formed in a form of a thin film while maintaining a shape conforming to the tip shape of the microneedle.

Then, the microneedle 1 according to Example 1 of the present disclosure was inserted into an agarose gel imitating the skin tissue. After a certain time has lapsed, the microneedle 1 was removed from the agarose gel, and then changes in the agarose gel and the microneedle 1 were identified.

FIG. 4b is a diagram to illustrate the microneedle according to Example 1 of the present disclosure, and is a photograph showing a surface of the agarose gel and a surface of the microneedle when inserting and removing the microneedle 1 according to Example 1 of the present disclosure into and from the agarose gel (scale bar; 500 μm).

Referring to FIG. 4b, it may be identified that when the microneedle 1 on which the coating layer of the hyaluronic acid has been formed is inserted into the agarose gel, the coating layer of the hyaluronic acid swells. In particular, it may be identified that when the microneedle 1 is removed from the agarose gel, the coating layer of the hyaluronic acid is left and dissolved in the agarose gel. Further, it may be identified that there is no residual coating layer on the surface of the microneedle 1 removed from the agarose gel. This means that in the microneedle 1 according to the present disclosure, the coating layer swells in the moisture in the agarose gel, and at the same time, the surface thereof rapidly dissolves in the moisture and thus the coating layer may be easily separated from the microneedle 1 and thus implanted into the skin tissue.

That is, it may be identified that according to the present disclosure, the implantable microneedle that may easily implant the coating layer into the body was manufactured. It may be identified that in the implantable microneedle according to the present disclosure, the coating layer may be quickly separated from the microneedle due to moisture and may be easily implanted into the body.

Further, after mounting the microneedle patch whose the tip surface was selectively plasma-treated on the stage and tilting the stage at an inclination angle of about 45°, a sucrose aqueous solution was dropped only on the tip of the microneedle using a dispenser. Then, the solution was dried at room temperature to form the sacrificial layer.

FIG. 5a is a diagram to illustrate a microneedle according to Example 2 of the present disclosure, and is a photograph showing the sacrificial layer obtained by dripping the sucrose aqueous solution on the selectively plasma-treated tip surface of the microneedle and drying the solution at room temperature.

Referring to FIG. 5a, it may be identified that the sacrificial layer solution (sucrose aqueous solution) (blue) dropped on the microneedle surface does not flow downwards along the microneedle and maintains a shape of the dropped shape thereof. It may be identified that after drying the solution at room temperature, the sacrificial layer is in close contact with the tip of the microneedle and is formed in the form of the thin film while maintaining a shape conforming to the tip shape of the microneedle.

Subsequently, a mixture (gelatin+genipin) of a gelatin solution and genipin a crosslinking agent was dropped on the sacrificial layer, and then dried at room temperature to form the coating layer. Thus, the microneedle (hereinafter, microneedle 2) according to Example 2 of the present disclosure was manufactured.

FIG. 5b is a diagram for illustrating the microneedle according to Example 2 of the present disclosure, and is a photograph showing the coating layer obtained by dropping the mixture (gelatin+genipin) on the sacrificial layer made of the sucrose and drying the mixture at room temperature.

Referring to FIG. 5b, it may be identified that after dripping the mixture (gelatin+genipin) on the blue sacrificial layer of the sucrose, the mixture does not flow downwards along the microneedle and maintains a shape of the dropped mixture solution. It may be identified that after drying the mixture solution at room temperature, the coating layer is formed in the form of a thin film and is in close contact with the tip of the microneedle while covering the sacrificial layer and maintaining a shape conforming to the tip shape of the microneedle.

That is, it may be identified that according to the present disclosure, the sacrificial layer and the coating layer may be formed only on the tip of the microneedle.

Further, FIG. 5c is a photograph showing a surface of the agarose gel and a surface of the microneedle when inserting and then removing the microneedle 2 having the sacrificial layer made of the sucrose and the mixture (gelatin+genipin) based coating layer formed thereon according to Example 2 of the present disclosure into and from the agarose gel imitating the skin tissue (scale bar; 500 μm).

Further, FIG. 5c shows the microneedle 2 according to Example 2 of the present disclosure, and is a photograph showing a surface of the agarose gel and a surface of the microneedle when inserting and then removing the microneedle 2 according to Example 2 of the present disclosure into and from the agarose gel (scale bar; 500 μm).

In FIG. 5c, (a) shows a picture at a certain time duration after inserting the microneedle 2 according to Example 2 of the present disclosure into the agarose gel, (b) shows a photo of the agarose gel after removing the microneedle 2 from the agarose gel, (c) shows a photo of a surface of the microneedle 2 removed from the agarose gel.

Referring to FIG. 5c, as shown in (a) in FIG. 5c, it may be identified that when the microneedle having the sucrose based sacrificial layer and the mixture (gelatin+genipin) based coating layer formed thereon is inserted into the agarose gel, the mixture (gelatin+genipin) based coating layer absorbs the moisture and swells. As shown in (b) of 5c, it may be identified that when the microneedle is removed from the agarose gel, the swelled mixture (gelatin+genipin) based coating layer is mechanically firmly engaged with the agarose gel and remains in the agarose gel while the microneedle is removed from the agarose gel. That is, it may be identified that the mixture (gelatin+genipin) based coating layer is separated from the microneedle, and accordingly, the mixture (gelatin+genipin) based coating layer is implanted in the agarose gel.

Further, referring to (c) of 5c, it may be identified that the sacrificial layer and the coating layer are not present on the surface of the microneedle removed from the agarose gel. This indicates that when the microneedle according to the present disclosure is inserted into the agarose gel, the sacrificial layer of sucrose is dissolved in moisture and thus a space is formed between the swelled mixture (gelatin+genipin) based coating layer and the microneedle, such that the mixture (gelatin+genipin) based coating layer may be easily separated from the microneedle while the mixture (gelatin+genipin) based coating layer is firmly fixed in the agarose gel via the swelling.

That is, it may be identified that the sacrificial layer and the coating layer may be easily formed only on the tip surface of the microneedle according to the present disclosure. It may be identified that when the microneedle according to the present disclosure is inserted into the skin, the coating layer swells in the moisture in the skin tissue and is firmly fixed to the skin tissue, and the sacrificial layer is dissolved in water. Thus, when removing the microneedle, the coating layer is separated therefrom and implanted into the tissue.

In addition, to describe the formation of the coating layer using gelatin, hyaluronic acid, chitosan, chondroitin sulfate as the coating layer forming polymer according to the present disclosure, a gelatin solution, a mixed solution of a hyaluronic acid-methacrylate and a photocrosslinker, a 600 k hyaluronic acid solution, a mixed solution of a hyaluronic acid (HA-SH) having a thiol group introduced thereto and genipine, a mixed solution of chitosan and genipine, a mixed solution of chondroitin sulfate and genipine were prepared as the swellable polymer solutions, respectively. Each solution was dropped on the sacrificial layer of sucrose as described with reference to the FIG. 3, and dried at room temperature.

As a result, it could be identified that after each solution was dropped, each solution did not flow down along the microneedle, and after drying each solution, the coating layer was adhered on the sacrificial layer and was coated in the form of the thin film.

In addition, in order to identify effects due to the varying shapes of the microneedle, a microneedle structure having a cone-shape was prepared. The microneedle was manufactured substantially in the same way as the microneedle was manufactured according to Example 1 of the present disclosure.

As a result, it may be identified that in the conical microneedle, a portion of the sacrificial layer solution flows downwards along the microneedle. Further, it may be identified that when forming the coating layer on the sacrificial layer, a portion of the coating layer solution flows downward along the microneedle.

In addition, it may be identified as shown in (c) of the FIG. 5 that when the microneedle 1 according to Example 1 of the present disclosure is inserted into the agarose gel and removed therefrom, the sacrificial layer is dissolved and the swellable coating layer is completely separated from the microneedle, so that the coating layer is fixedly located in the agarose gel and only the microneedle is removed from the agarose gel. However, it may be identified as shown in (c) of the FIG. 5 that when the conical microneedle is inserted into the agarose gel and then is removed therefrom, the swellable polymer based coating layer is somewhat removed from the agarose gel. That is, it may be identified that the shape of the microneedle structure is preferably a shape such as a bullet.

Therefore, in summary, it may be identified that according to the examples according to the present disclosure, the microneedle is realized in which the coating layer may be easily formed only on the tip of the microneedle, and when the microneedle is inserted into the body and then is removed therefrom, the coating layer may be easily separated from the microneedle and thus may be implanted into the body.

Further, in particular, referring to FIG. 4a to FIG. 5c, it may be identified that forming the sacrificial layer and the coating layer while the microneedle structure is tilted at a predetermined inclination may allow the sacrificial layer and the coating layer on the tip surface of the microneedle in an asymmetrical manner in which a larger amount thereof is formed on one portion thereof than on the other portion thereof. This means that the swellable polymer based coating layer having the asymmetric coating structure may be more firmly fixed in the agarose gel.

In addition, the implanted coating layer may carry the drug and may release the drug when dissolving in the water. Accordingly, it may be identified that the microneedle according to the present disclosure may be used as implantable drug delivery means or an implantable tissue adhesive due to the robust mechanical fixation of the swellable coating layer in the tissue.

The present disclosure has been described with reference to the preferred embodiments of the present disclosure. Those skilled in the art will understand that the present disclosure may be variously modified and changed without departing from the spirit and scope of the present disclosure as described in the following claims.

REFERENCE NUMERALS

100: Microneedle
120: Microneedle tip
122: Sacrificial layer
124: Coating layer
200: Patch portion
300: Microneedle patch

What is claimed is:

1. A method for manufacturing a microneedle having a coating layer on a surface of a tip, the method comprising:
   dripping a swellable polymer solution on the tip of the microneedle to form the coating layer thereon;
   wherein the method further comprises, before forming the coating layer, coating a sacrificial layer solution on a surface of the tip of the microneedle to form a sacrificial layer thereon,
   wherein forming the coating layer includes dripping the swellable polymer solution on the sacrificial layer to form the coating layer thereon, wherein the sacrificial layer has been dissolved in water before the swellable polymer based coating layer has been dissolved in water.

2. The method of claim 1, wherein the dripping of the swellable polymer solution is performed while the microneedle is tilted at an angle greater than 0° and smaller than 90° with respect to a ground.

3. The method of claim 1, wherein forming the coating layer includes forming the coating layer having an asymmetrical structure with respect to a central axis of the microneedle.

4. The method of claim 3, wherein the coating layer is thicker as the coating layer extends downwardly.

5. The method of claim 1, wherein the swellable polymer solution contains at least one polymer selected from a group consisting of gelatin, chitosan, collagen, hyaluronic acid and chondroitin sulfate.

6. The method of claim 1, wherein the microneedle has a shape having a cylindrical body and a conical tip.

7. The method of claim 6, wherein in forming the coating layer, a difference between an inclination of a surface of the body and an inclination of a surface of the tip allows the dripped swellable polymer solution to be prevented from flowing downward along the body of the microneedle.

8. The method of claim 1, wherein in forming the coating layer, at least a portion of a surface of the sacrificial layer is temporarily dissolved in the dripped swellable polymer solution to prevent the swellable polymer solution from flowing downwards along the microneedle, such that the coating layer is formed only on the sacrificial layer.

9. The method of claim 8, wherein the sacrificial layer solution contains at least one of a monosaccharide or a water-soluble polymer having a molecular weight lower than 10k.

10. An implantable microneedle comprising:
a tip; and
a swellable polymer based coating layer covering at least a portion of a surface of the tip,
wherein the coating layer is removable from the microneedle in a body environment;
wherein the implantable microneedle further comprises a sacrificial layer disposed between the surface of the tip of the microneedle and the swellable polymer based coating layer, wherein the sacrificial layer covers at least a portion of the tip surface of the microneedle, wherein the sacrificial layer has been dissolved in moisture before the swellable polymer based coating layer has been dissolved in moisture,
wherein the coating layer covers at least a portion of the sacrificial layer.

11. The implantable microneedle of claim 10, wherein the swellable polymer includes at least one selected from a group consisting of gelatin, chitosan, collagen, hyaluronic acid and chondroitin sulfate.

12. The implantable microneedle of claim 11, wherein the swellable polymer is crosslinked to a degree such that at least a portion of an interface or a surface thereof is dissolved in a short time in moisture.

13. The implantable microneedle of claim 10, wherein the microneedle has a shape having a cylindrical body and a conical tip.

14. The implantable microneedle of claim 10, wherein the coating layer has an asymmetrical structure with respect to a central axis of the microneedle.

15. The implantable microneedle of claim 14, wherein the coating layer has one portion thicker than the other portion thereof.

16. The implantable microneedle of claim 10, wherein the sacrificial layer is made of at least one of a monosaccharide or a water-soluble polymer having a molecular weight lower than 10k.

17. The implantable microneedle of claim 10, wherein when inserting the microneedle into the body and removing the microneedle therefrom, the coating layer is separated from the microneedle and thus is implanted in the body.

18. The implantable microneedle of claim 10, wherein the coating layer contains a drug therein.

19. The implantable microneedle of claim 18, wherein the microneedle acts as implantable drug delivery means or an implantable tissue adhesive.

\* \* \* \* \*